United States Patent [19]

Hess et al.

[11] Patent Number: 4,660,571

[45] Date of Patent: Apr. 28, 1987

[54] PERCUTANEOUS LEAD HAVING RADIALLY ADJUSTABLE ELECTRODE

[75] Inventors: Stanley R. Hess; Terri Kovacs, both of Miami, Fla.

[73] Assignee: Cordis Corporation, Miami, Fla.

[21] Appl. No.: 756,756

[22] Filed: Jul. 18, 1985

[51] Int. Cl.[4] ............................................. A61N 1/04
[52] U.S. Cl. .................................... 128/784; 128/786; 604/105
[58] Field of Search ............... 128/639, 642, 656, 657, 128/658, 772, 774, 419 D, 419 S, 783, 784, 786, 303.14, 303.15, 303.11, 303.12, 362, 395, 397, 398; 604/105, 20

[56] References Cited

U.S. PATENT DOCUMENTS 4,419,819 12/1983 Dickhudt et al. ............... 128/419 D
4,517,974 5/1985 Tanner ........................... 128/303.14

FOREIGN PATENT DOCUMENTS 0009732 9/1979 European Pat. Off. ............ 128/786
8002231 10/1980 European Pat. Off. ............ 128/786
2513868 3/1975 Fed. Rep. of Germany ...... 128/786

OTHER PUBLICATIONS

R. E. Johnston et al, *Body Tissue Transducer,* Jan. 1964, pp. 13-14 of vol. 6, No. 8 of IBM Technical Disclosure Bulletin.

*Primary Examiner*—Edward M. Coven
*Attorney, Agent, or Firm*—Lockwood, Alex, Fitzgibbon & Cummings

[57] ABSTRACT

A disposable percutaneous lead is provided which is suitable for caring out a variety of functions, including endocardial functions of mapping, ablation and/or pacing. The percutaneous lead maintains a substantially isodiametric profile for insertion through a body cavity such as a vein or artery. By manipulation of a proximal end portion of the device, elongated peripheral segments of the distal end portion of the device move generally radially outwardly in order to provide a plurality of radially adjustable electrodes for forming a mapping array. An elongated shaft structure is also provided for ablation purposes, while electrodes for pacing are also available on the device.

10 Claims, 7 Drawing Figures

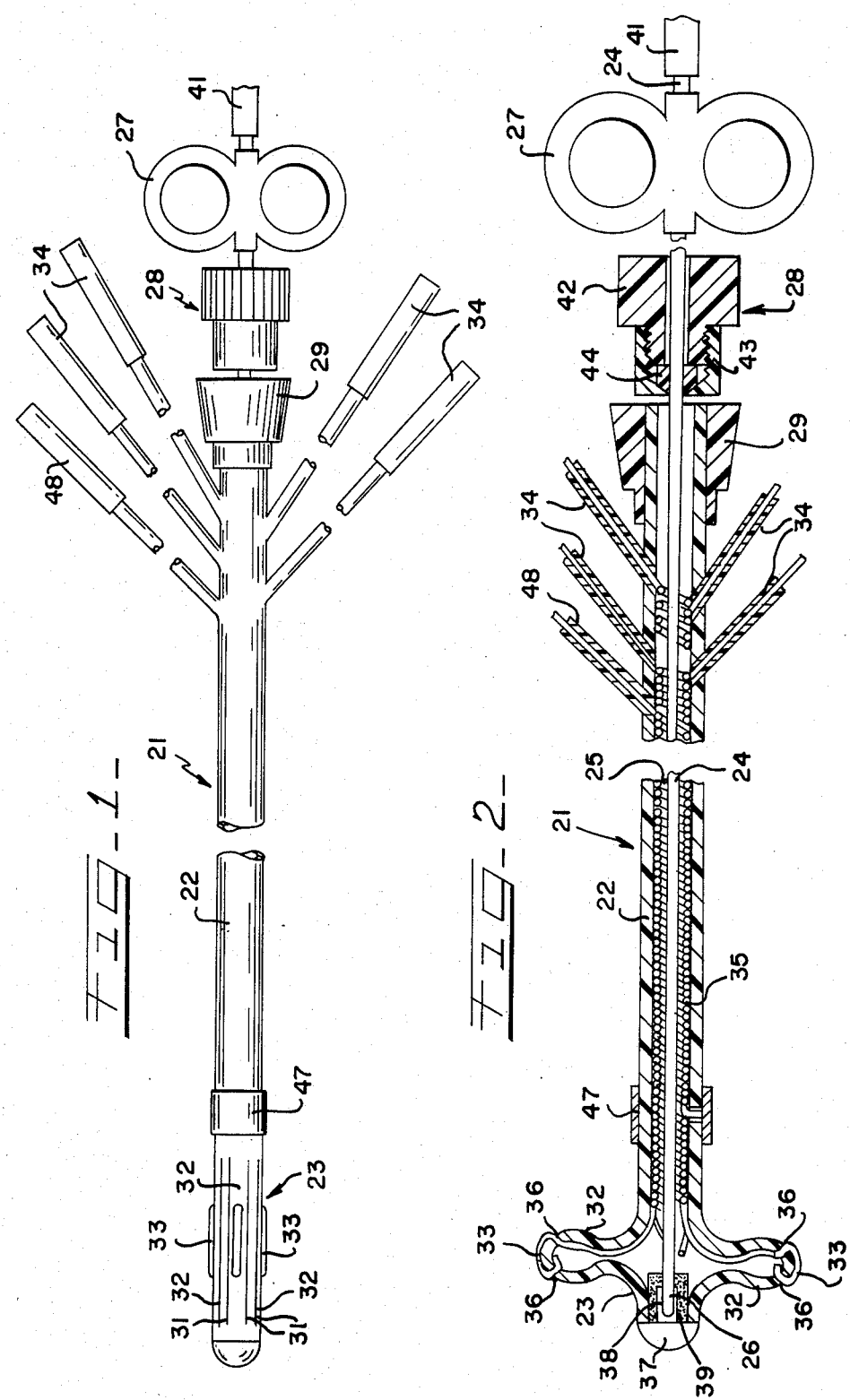

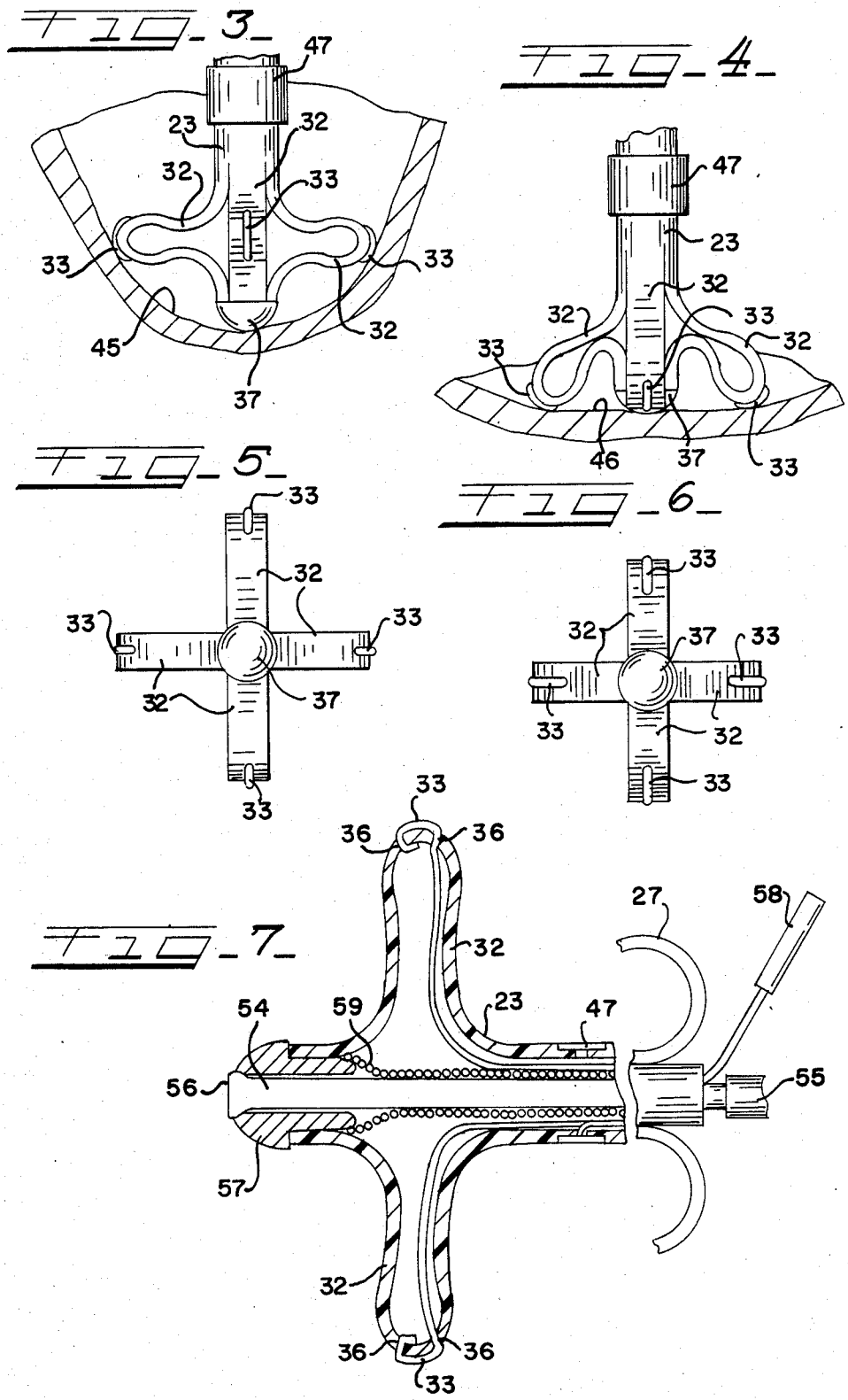

PERCUTANEOUS LEAD HAVING RADIALLY ADJUSTABLE ELECTRODE

BACKGROUND AND DESCRIPTION OF THE INVENTION

This invention generally relates to percutaneous leads for performing one or more of mapping pacing, or ablation, the percutaneous lead being particularly well suited for performing these functions in association with the treatment of cardiac conditions, and it lends itself particularly well for use as a disposable, temporary treatment device.

While the lead is substantially isodiametric when it is being passed through a narrow body passageway such as a vein or an artery, the distal end portion of the percutaneous lead preferably includes a plurality of elongated slits that are spaced from each other around the circumference of the distal end portion in order to define at least one elongated peripheral segment having an electrode, which elongated peripheral segment is adjustable to the extent that it folds substantially upon itself in order to generally radially move its electrode outwardly. This adjustability feature of the device is such that the elongated slit and its electrode are readily returned to an orientation that is substantially isodiametric with the remainder of the percutaneous lead. When desired, a plurality of such adjustable elongated peripheral segments are provided.

Electrophysiological studies and treatments of patients have in the past utilized many different devices and systems, including those that incorporate the use of an elongated percutaneous lead that provides an electrically conductive elongated pathway between a location that is external of the patient and a location within the patient at which sensing, stimulation or treatment is to take place. When this percutaneous route is taken in conjunction with studies or treatment of the heart, this is known as an endocardial approach. While an epicardial approach is possible, this is not always the most suitable procedure since it requires thoracotomy and the exposure of the heart.

When the study or treatment to be performed includes mapping and/or ablation, such procedures require accurate identification of the focus or foci by recording the electrical signals generated by the cardiac tissue at specific locations. Once identified, each focus is ablated or fulgurated. It is highly desireable, if not mandatory, to ablate the abnormal source in an accurately circumscribed location in order to minimize damage to normal tissue that is adjacent to the area of the anomalous tissue. Often, such accurate location is substantially enhanced when the epicardial approach is used rather then the substantially less intrusive endocardial approach.

Accordingly, there is a need for a device that has the attributes of the less intrusive endocardial approach while still providing substantial control and adjustability on the order of that possible by the epicardial approach so that the endocardial approach is more feasible for studies and treatments including those involving any or all of mapping, destruction, or pacing functions.

With more particular reference to these functions, the pacing function is well-known in the art, whereby an electrical impulse is imparted to a particular location of the body in order to either assist proper functioning of a body organ or in order to control or bring under control an iatrogenic or spontaneous dysrhythmia by pacing a ventrical or in order to stimulate or pace the heart so as to assist in mapping its electrical pathways. Currently available so-called pacing leads can accomplish these functions in an endocardial manner by receiving appropriate impulses from a pacer device that is external of the body. Typically, these devices are capable of performing only this pacing function.

Regarding the mapping function, such is undertaken to identify specific foci or anatomical locations which, for example, are a source of abnormal cardiac rhythm in patients with dysrhythmias. Mapping electrode sets for epicardial or endocardial mapping of heart signals have been provided in the past. Typically, these mapping electrode sets are utilized during cardiac surgery in order to sense the cardiac signal and report it to the surgical team through appropriate display and/or print out devices. The surgical team may observe the reported data and immediately utilize same in connection with a surgical procedure, or the data may be collected for subsequent analysis. Such mapping involves timing that is based upon the leading edge of an excitation wave through conductive tissue, such as that of the heart. Generally, mapping procedures include the induction of tachycardia while the mapping electrode set is in place, which means that mapping speed and efficiency are important during these procedures.

The ablation function is typically performed in association with the mapping function. Once the specific foci or anatomical locations are pinpointed by mapping or the like, each such location can be subjected to ablation or fulguration in order to, in effect, destroy the target focus or location, which for example, is the source of an abnormal cardiac rhythm. Unless the ablation function is carried out in close association with the mapping function, it is exceedingly difficult to achieve the ablation accuracy which is necessary to avoid or minimize damage to normal or undiseased tissue that is adjacent to the anomalous, damaged or diseased tissue to be destroyed by the ablation procedure.

When one attempts to carry out the mapping function and/or the ablation function by an endocardial approach, mapping accuracy, speed and efficiency are typically quite difficult to achieve since the mapping device must pass through a narrow body passageway such as a vein or an artery. Often, electrodes of a device for carrying out endocardial mapping provide mapping electrodes that are generally stationarily mounted with respect to each other, whereby it is difficult to substantially modify the mapping surface, a situation that is further complicated by the requirement of fluoroscopic guidance for placement of mapping electrodes and, for that matter, of the ablation tip of an endocardial ablation device or catheter.

Another exceptionally desirable feature for a mapping device is to provide it with an electrode array by which the electrodes of the array can simultaneously engage the surface being mapped. When the endocardial approach is undertaken, the surfaces being mapped usually will be concave or generally flat. Unless the electrodes of the mapping electrode set exhibit some degree of adjustability, it is not possible to have the same device map such a variety of surface configurations. This type of adjustability is rendered more difficult when such must be provided for an endocardial device which, ideally, should be substantially isodiametric throughout the length of the device.

There is accordingly a need for a device that can achieve endocardial mapping or other percutaneous procedures, which device is a substantially isodiametric catheter-type of device that has a distal end portion having an electrode that is location-adjustable when the device is at or near its percutaneous target location, which adjustment is carried out by manipulation of a suitable assembly that is external of the body.

These various desirable attributes are achieved by the present invention, which provides a percutaneous lead having an elongated body and an elongated shaft slideably mounted within the body, with the respective distal end portions of the elongated body and of the elongated shaft being operatively connected to each other. The distal end portion of the elongated body is substantially isodiametric with the rest of the body and has a plurality of elongated slits that are spaced from each other along the circumference of the distal end portion of the body in order to define at least one elongated peripheral segment of the body distal end portion. An electrode is positioned on the elongated peripheral segment. When the elongated body and/or the elongated shaft are slidingly moved with respect to the other, which relative movement includes either or both of movement of the body in a distal direction or movement of the shaft in a proximal direction, the elongated peripheral segment generally folds onto itself in a substantially outwardly directed manner to thereby move the electrode thereof to a location that is no longer isodiametric with respect to the elongated body. Relative movement of the elongated body and/or elongated shaft in substantially opposite directions returns the elongated peripheral segment and its electrode to its initial, substantially isodiametric configuration.

It is accordingly a general object of the present invention to provide an improved percutaneous lead that exhibits adjustability between isodiametric and outwardly extending electrode configurations.

Another object of the present invention is to provide an improved percutaneous lead that is capable of performing mapping, ablation and/or pacing without having to remove the lead from its percutaneous location.

Another object of this invention is to provide an improved percutaneous lead that functions in the manner of an endocardial catheter that can be guided through a narrow body passageway such as a vein or an artery when it has a substantially isodiametric configuration but which can, after it has been properly positioned within the body, be manipulated such that distal electrodes thereof expand radially outwardly.

Another object of this invention is to provide a torque-controlled temporary pervenous lead having recording electrodes for mapping of endocardial electrophysiological signals, having electrodes for unipolar or bypolar pacing, and having ablating capabilities.

Another object of the present invention is to provide an endocardial lead having a multiple electrode array for mapping plane or concave internal surfaces.

Another object of this invention is to provide an endocardial mapping lead that has an electrode array for precise location of the ablation electrodes and by also recording from a central or tip electrode in order to permit identification of excitation propagation.

Another object of this invention is to provide an improved percutaneous lead that is a relatively inexpensive and disposable.

Another object of the present invention is to provide an improved percutaneous lead having laser-conducted ablation.

These and other objects, features and advantages of this invention will be clearly understood through a consideration of the following detailed description.

BRIEF DESCRIPTION OF THE DRAWINGS

In the course of this description reference will be made to the accompanying drawings wherein:

FIG. 1 is an elevational view, partially broken away, of the percutaneous lead according to this invention;

FIG. 2 is an elongated substantially cross-sectional view through a percutaneous lead according to this invention such as that illustrated in FIG. 1;

FIG. 3 is a detailed view of the distal end portion of the device shown in FIG. 2 that is at a configuration for mapping a concave endocardial surface;

FIG. 4 is a detailed view of the distal end portion of the device shown in FIG. 2 that is at a configuration for mapping a substantially planar endocardial surface;

FIG. 5 is a distal end view of the device at its orientation that is illustrated in FIG. 3;

FIG. 6 is a distal end view of the device at its orientation that is illustrated in FIG. 4; and FIG. 7 is a broken-away generally cross-sectional view of an alternative embodiment incorporating laser-conducted ablation.

DESCRIPTION OF THE PARTICULAR EMBODIMENTS

Percutaneous lead, generally designated as 21 in FIG. 1, includes an elongated body 22 that is substantially isodiametric throughout its length and which includes a distal end portion, generally designated as 23. An elongated shaft 24 is positioned within a hollow core 25 of the elongated body 22. Distal end portion 26 of the elongated shaft 24 is operatively attached to the distal end portion 23 of the elongated body 22, while the proximal end portion of the elongated shaft 24 has a handle assembly 27 secured thereto in order to facilitate relative movement between the elongated shaft 24 and the elongated body 22. A locking assembly 28 can be provided in order to fix the location of the elongated shaft 24 with respect to the elongated body 22 after such relative movement has been carried out. A hub 29 may be fused to the proximal end of the elongated body 22.

In order to most advantageously impart percutaneous properties to the lead 21, the elongated body 22 may be in the nature of a torque-controlled catheter so as to facilitate and assist in directing passage of the percutaneous lead 21 through a body cavity such as a vein or an artery. Additionally, the elongated shaft 24 can assist in provided torque-controlled properties to the percutaneous lead 21 by being made of a material and by being sized such that the elongated shaft 24 is substantially non-compressable in an axial direction while being moderately bendable in a generally transverse direction.

With more particular reference to the distal end portion 23 of the elongated body 22, such includes a plurality of elongated longitudinal slits 31 that are spaced from each other along the circumference of the distal end portion 23 in order to thereby define at least one elongated peripheral segment 32. An electrode 33 is mounted within or on each elongated peripheral segment 32, and each such electrode 33 is in electrical communication with a terminal assembly 34 projecting from the proximal end portion of the elongated body 22.

In the preferred arrangement illustrated, this electrical communication is provided by a multifilar coil 35 of insulated stainless steel wire or the like. Also according to the preferred structure, each electrode 33 is formed by stripping away the insulation of a strand of the coil 35 and having that stripped-away portion project through one or more holes 36 through each elongated peripheral segment 32. Each of the terminal assemblies 34 is adapted for interconnecting to a suitable recording device (not shown).

In the embodiment illustrated in FIG. 2, a tip electrode 37 is mounted at the distal end of the elongated body 22. A tip electrode at 37 includes an internal stem 38 for attachment to the distal end portion 26 of the elongated shaft 24, which in this embodiment is an electrically conductive member such as a stainless steel wire. A seal 39 is preferably provided in order to substantially prevent leakage around the tip electrode 37. A terminal assembly 41 is included at the proximal end of the elongated shaft 24 for ease of connection to the mapping recording instrument (not shown) or to a fulgurating device such an electrocautery device (not shown). In this embodiment, the elongated shaft 24 is a conductive wire which, along with the tip electrode 37, are designed to withstand the delivery of 400 Joules of electrical energy from a suitable device (not shown) and into the tissue without loss of material or function.

Locking assembly 28 can be of known construction, such as that of a Touhy Borst adaptor. The device illustrated in FIG. 2 includes a hub 42 having an externally threaded portion that is fitted with a rotatable collar 43 that engages an internal grommet 44 which frictionally engages and grips the elongated shaft 24 upon rotation of the collar 43 with respect to the hub 42. Collar 43 abuts against the proximal end of the elongated body 22 and/or its hub 29 in order to prevent further movement of the elongated shaft 24 into hollow core 25 of the elongated body 22.

When the elongated shaft 24 and/or the elongated body 22 are moved relative to each other, each elongated peripheral segment 32 is modified in its configuration. With the lead 21 in the configuration illustrated in FIG. 1, each elongated peripheral segment 32 is substantially isodiametric with the rest of the elongated body 22. Effecting such relative movement until an additional length of elongated shaft 24 projects beyond the proximal end of the elongated body 22 causes each elongated peripheral segment 32 to buckle or fold onto itself and develop a generally outwardly directed radial movement thereof and of the electrode 33 supported thereby. Such movement to the mapping orientation illustrated in FIGS. 2, 3 and 5 is especially appropriate for mapping a concave configuration such as that of the cardiac cavity 45 shown in FIG. 3.

Continued relative movement of the elongated body 22 and the elongated shaft 24 so as to proceed with additional movement of the elongated shaft 24 out of the elongated body 22 results in a mapping configuration such as that illustrated in FIGS. 4 and 6, which is particularly suitable for mapping generally planar surfaces 46 as shown in FIG. 4. Achieving the configuration shown in FIG. 4 can be facilitated by positioning each electrode 33 along the elongated peripheral segment 32 at a location that is not centrally located on the elongated peripheral segment 32, but is at a location distal thereof.

Distal end portion 23 may further include a ring electrode 47. Electrode 47 is in electrical communication with a suitable conductor such as a wire of the multifilar coil 35 which is in electrical communication with a terminal assembly 48 for connection to a suitable device, which may be either the recording device (not shown) or the electrocautery device (not shown) discussed hereinabove.

In the preferred arrangement illustrated in the drawings, the percutaneous lead 21 includes four elongated peripheral segments 32 and four respective electrodes 33 which are substantially equally circumferentially spaced apart and which are generally equidistant from the distal tip electrode 37 and/or the ring electrode 47. These four electrodes are sensing or mapping electrodes, and they provide a mapping electrode array.

In the embodiment illustrated in FIG. 7, the ablation capabilities are provided by a system incorporating the use of laser energy. In this embodiment, the elongated shaft is an optical fiber 54 that passes through an axial bore of a tip electrode 57. Laser energy is transmitted through the optical fiber 54 by way of a terminal 55 for connection to a laser device (not shown), and the optical fiber 54 transmits this laser energy therethrough and to an ablation surface 56 thereof. The tip electrode 57 is connected to a suitable terminal assembly 58 by means of a conductor or wire 59.

Exemplary operation and use of the percutaneous lead 21 according to this invention includes subcutaneous introduction into a vein for advancement to the right ventricle or to the right atrium of the heart of a cardiac patient. Advancement through an artery would be needed for placement into the left ventricle. During such advancement procedure, the lead 21 will be in its isodiametric configuration such as that illustrated in FIG. 1, and gross positioning of the lead 21 to near the desired site is accomplished by fluoroscopy. Fine positioning of the lead is accomplished by sensing the electrical potential at each electrode 33, typically in association with either the tip electrode 37 or the ring electrode at 47 as a reference.

When the general area of interest is located, the elongated shaft 24 and the elongated body 22 are moved relative to each other such that the elongated shaft increases in its projection beyond the proximal end of the elongated body 22, at which time each elongated peripheral segment 32 buckles onto itself until the desired degree of angulation of the segment 32 is achieved and until each electrode 33 is radially extended and positioned as desired. After the desired position is achieved, the locking assembly 28 may be manipulated in order to maintain that positioning. Typically, a suitable electrode array will be formed and can be moved from one endocardial site to another until each abnormal focus is located. Once this focus is located by this mapping procedure, it can be ablated by the passage of a fulgurating current through the elongated shaft 24 and to the tip electrode 37, or, when the embodiment of FIG. 7 is utilized, the abnormal focus can be ablated by use of a laser power source through the optical fiber 54 and its ablation surface 56.

In sensing or mapping of the endocardial surface in this example, the array of electrodes 33 and the tip electrode 37 can be utilized to provide a configuration of five seperate recording, mapping or sensing sites, with four of them forming a square and the fifth being the center point. In addition, various combinations of pairs can be achieved utilizing these five electrodes to determine the direction of propagation of the electrical activity and the activation sequence of the cardiac tissue under study. Terminal assemblies 34, 41 and 48 are connected to recording or display instrumentation in the sequence needed to display either from single electrodes 33 referenced to ring electrode 47 or from chosen pairs of electrodes. If it is found necessary either to control a dysrythmia by pacing or to stimulate the ventricles, the tip electrode 37 and the ring electrode 47 can be utilized as a bipolar electrode configuration. Lead 21 can also be utilized in the unipolar configuration by disconnecting the ring electrode 47 from the external pacing unit and substituting an electrode on the elongated body 22 as an anode, which must be connected to the other pole of an external pacer (not shown).

It will be understood that the embodiments of the present invention which have been described are illustrative of some of the applications of the principles of the present invention. Numerous modifications may be made by those skilled in the art without departing from the true spirit and scope of the invention.

We claim:

1. A percutaneous endocardial lead comprising:
   an elongated body member having an elongated hollow core therewithin, a proximal end portion, and a distal end portion;
   an elongated shaft member slidingly mounted within said elongated hollow core of the body member, said elongated shaft member having a proximal end portion and a distal end portion, and said shaft member distal end portion being operatively connected to said distal end portion of the elongated body member;
   a tip electrode at said distal end portion of the elongated shaft member and in electrical communication with said proximal end portion of the elongated body member;
   a plurality of elongated peripheral segments at the distal end portion of the elongated body member;
   a plurality of elongated conductors, each extending between each of said elongated peripheral segments and said proximal end portion of the elongated body member, said elongated conductors being insulated from each other;
   mapping electrode means including a plurality of electrodes, each said electrode being on each said elongated peripheral segment, each said electrode being in electrical communication with one of said elongated conductors, and said electrodes of the mapping electrode means provide an electrode array generally around the tip electrode;
   means for adjusting said electrode array between a closed configuration that is substantially isodiametric with said elongated body member and open configurations at which each elongated peripheral segment folds on itself and moves each electrode to an outwardly directed location including to a location generally coplanar with said tip electrode;
   said means for adjusting said electrode array including said elongated body member and said elongated shaft member slidingly mounted therewithin, whereby said elongated body member and said elongated shaft slidingly move relative to each other in order to adjust said electrode array between said closed configuration and said open configurations; and
   ablation means having an ablation surface generally at said tip electrode, said ablation surface being generally circumscribed by said electrode array at said open configurations thereof.

2. The percutaneous lead according to claim 1, wherein said distal end portion of the elongated body member includes a plurality of elongated slits that are spaced from each other along the circumference of said distal end portion in order to define said elongated peripheral segments.

3. The percutaneous lead according to claim 1, further including a handle assembly mounted onto said proximal end portion of the elongated shaft member.

4. The percutaneous lead according to claim 1, further including a locking assembly in order to secure a selected relative position of said elongated body member with respect to said elongated shaft.

5. The percutaneous lead according to claim 1, wherein said elongated conductor and said electrode are of a continuous unitary structure, and said electrode is formed by passing a portion of said elongated conductor through said elongated peripheral segment.

6. The percutaneous lead according to claim 1, wherein said elongated shaft member is an electrical conductor.

7. The percutaneous lead according to claim 1, wherein said tip electrode is operatively secured to said elongated shaft member, said elongated shaft member providing electrical communication between the tip electrode and the proximal end portion of the elongated body member.

8. The percutaneous lead according to claim 1, wherein said elongated shaft member is an optical fiber having a distal end at which said ablation surface is located.

9. The percutaneous lead according to claim 1, wherein said tip electrode is a component of a pacing means.

10. The percutaneous lead according to claim 1, wherein said elongated body member is a torque-controlled catheter that is substantially non-compressable in an axial direction and moderately bendable in a generally transverse direction.

* * * * *

UNITED STATES PATENT AND TRADEMARK OFFICE
CERTIFICATE OF CORRECTION

PATENT NO. : 4,660,571
DATED : April 28, 1987
INVENTOR(S) : Stanley R. Hess and Terri Kovacs It is certified that error appears in the above—identified patent and that said Letters Patent is hereby corrected as shown below:

In the ABSTRACT, line 2, "caring" should read --carrying--.
Column 1, line 54, "then" should read --than--.
Column 3, line 67, delete "a".
Column 6, line 63, "seperate" should read --separate--.

Signed and Sealed this

Fifteenth Day of December, 1987

Attest:

DONALD J. QUIGG

*Attesting Officer*     *Commissioner of Patents and Trademarks*